United States Patent
Psaros

Patent Number: 5,845,633
Date of Patent: Dec. 8, 1998

[54] DOSING DEVICE FOR ADDING A CONTROLLED AMOUNT OF A GAS TO A FLUID

[75] Inventor: Georgios Psaros, Tullinge, Sweden

[73] Assignee: Siemens Elema A.B., Solna, Sweden

[21] Appl. No.: 754,155

[22] Filed: Nov. 22, 1996

[30] Foreign Application Priority Data

Dec. 1, 1995 [SE] Sweden .................................. 9504310

[51] Int. Cl.$^6$ .................................................. A61M 15/00
[52] U.S. Cl. .............................. 128/200.24; 128/203.12; 128/203.25
[58] Field of Search .................. 128/200.24, 200.25, 128/203.12, 203.25, 205.11

[56] References Cited

U.S. PATENT DOCUMENTS

| | | | |
|---|---|---|---|
| 3,318,306 | 5/1967 | Strauss | 128/200.25 |
| 3,369,343 | 2/1968 | Robb | 128/200.25 |
| 3,634,053 | 1/1972 | Klass et al. | |
| 3,656,276 | 4/1972 | Vind | 128/200.25 |
| 3,833,016 | 9/1974 | Lucero et al. | |
| 3,854,894 | 12/1974 | Klass et al. | |
| 4,179,364 | 12/1979 | Bratten et al. | 210/321 B |
| 4,865,845 | 9/1989 | Eckenhoff et al. | 424/424 |
| 4,896,664 | 1/1990 | Harayama | 128/200.25 |
| 4,920,060 | 4/1990 | Parrent, Jr. et al. | 436/178 |
| 4,969,872 | 11/1990 | Urquhart et al. | 604/85 |
| 5,158,584 | 10/1992 | Tamura | 55/158 |

FOREIGN PATENT DOCUMENTS

| | | | |
|---|---|---|---|
| 0 005 866 | 12/1979 | European Pat. Off. | 128/200.25 |
| 0 048 943 | 9/1981 | European Pat. Off. | |
| 0 081 118 | 6/1983 | European Pat. Off. | 128/200.25 |
| 0 659 445 | 11/1994 | European Pat. Off. | |

*Primary Examiner*—Aaron J. Lewis
*Attorney, Agent, or Firm*—Hill & Simpson

[57] ABSTRACT

In a dosing device and method for controlled dosing of a first gas into a second gas or liquid membrane which is permeable to the first gas separates the first gas from the second gas or liquid. Dosing of the first gas is performed by controlling diffusion through the membrane. The size of the active diffusion area can be regulated by a barrier which is moveable in relation to the membrane. When the barrier is moved in relation to the membrane, a larger or smaller part of the membrane's diffusion area can be exposed to the second gas or liquid. Alternatively, the membrane's permeability can be controlled or the partial pressure of the first gas can be controlled.

32 Claims, 5 Drawing Sheets

DOSING DEVICE FOR ADDING A CONTROLLED AMOUNT OF A GAS TO A FLUID

BACKGROUND OF THE INVENTION

1. Field of the Invention

The present invention is directed to a dosing device for adding a controlled amount of gas to a fluid (i.e., a liquid or another gas), and more specifically is directed to a dosing device for adding a controlled amount of nitric oxide (NO) to a fluid to be administered to a patient.

2. Description of the Prior Art

In very small quantities, NO can have a number of beneficial effects on pulmonary function. Doses can range from about 1 ppm of NO up to about 50 ppm of NO, however, a problem is that NO is inherently hazardous and contributes to an increase in the conversion of NO into $NO_2$ on contact with oxygen. $NO_2$ is a highly toxic gas, even in very low concentrations. A number of designs for delivery and monitoring devices have been proposed for minimizing the risk to patients receiving NO. Monitoring is particularly difficult, since no methods are known for rapid and reliable measurement of low concentrations of NO.

SUMMARY OF THE INVENTION

An object of the invention is to provide a method and dosing device for delivering small amounts of gas, NO in particular, into a breathing gas supplied to a patient for medical purposes.

The above object is achieved in accordance with the principles of the present invention in a method and a dosing device wherein the gas to be added in a controlled amount to the fluid is separated from the fluid by at least one membrane, the membrane having an active diffusion area through which the gas must diffuse in order to reach the fluid. Diffusion of the gas through the membrane is actively controlled, thereby also controlling the amount of the gas which is added to the fluid.

The use of a material permeable to oxygen for increasing the oxygen content of a chamber is known, as described in U.S. Pat. No. 5,158,584 and which has a number of tubes arranged in a tube surrounding a chamber. The tubes are made of a material more permeable to oxygen than to nitrogen. The ends of the tubes are open to ambient air. A fan forces air through the tubes. When gas passes the tubes, oxygen diffuses more rapidly than nitrogen through the membrane into the chamber. The amount of oxygen in the chamber air is accordingly increased somewhat, compared to ordinary air. Air enriched with oxygen can then be respirated by a patient.

Similar systems are also used to oxygenate blood in an artificial lung. Blood is then allowed to pass through tubes of similar material, and oxygen is supplied to the exterior of the tubes. The oxygen diffuses into the blood, and carbon dioxide diffuses out in the opposite direction. This results in a gas exchange like the one occurring in an ordinary lung. One such apparatus is described in European Application 0 048 943.

Another use for a material permeable to gas is in the dehumidification of dehumidification of gases. A moist gas is fed through a system of tubing made from a material permeable to moisture. Moisture then diffuses into ambient air. The effect can be enhanced if the tubing is enclosed in a container through which a dry and hot gas is passed.

Neither of these known uses of semipermeable materials includes controlled dosing of a first gas into a second gas.

The dosing device according to the invention utilizes active control of diffusion. This can be achieved in a number of ways.

A first technique is to vary the active diffusion area, i.e. the area through which the area through which the first gas is to diffuse. In one embodiment according to the invention, the membrane is combined with a barrier. This barrier is made of a material which is impermeable to the first gas. The membrane and the barrier are arranged so they can move in relation in relation to each other. A major or minor part of the membrane can then be exposed to diffusion.

A second approach is to vary the membrane's permeability. In one embodiment of the dosing device according to the invention, the membrane has a number of coatings with varying permeabilities to the first gas. The coatings can be arranged so one coating at a time serves as the diffusion area, diffusion then depending on the choice of material. One or a number of coatings can be applied, in whole or part, to a basic coating in order to vary diffusion.

A third technique is to vary the partial pressure of the first gas, thereby causing more molecules to diffuse when the partial pressure rises and fewer molecules to diffuse when the partial pressure falls.

Additional versions can be obtained by combining the above embodiments.

The dosing device according to the invention is, as described above, particularly advantageous for use for dosing NO into a breathing gas.

Use of a dosing device according to the present invention eliminates the need for complicated monitoring. Since diffusion through the membrane is physically limited, in relation to the exposure area and relative pressure conditions, dosing can be performed with inherent safety since the maximum dose is limited. In particular, the concentration of NO in the dosing device can be limited so the patient only receives a harmless amount of NO, even if the entire diffusion area of the membrane is exposed to diffusion into the breathing gas. In principle, monitoring with a concentration meter will then be unnecessary.

DESCRIPTION OF THE PREFERRED EMBODIMENTS

Figure 1:
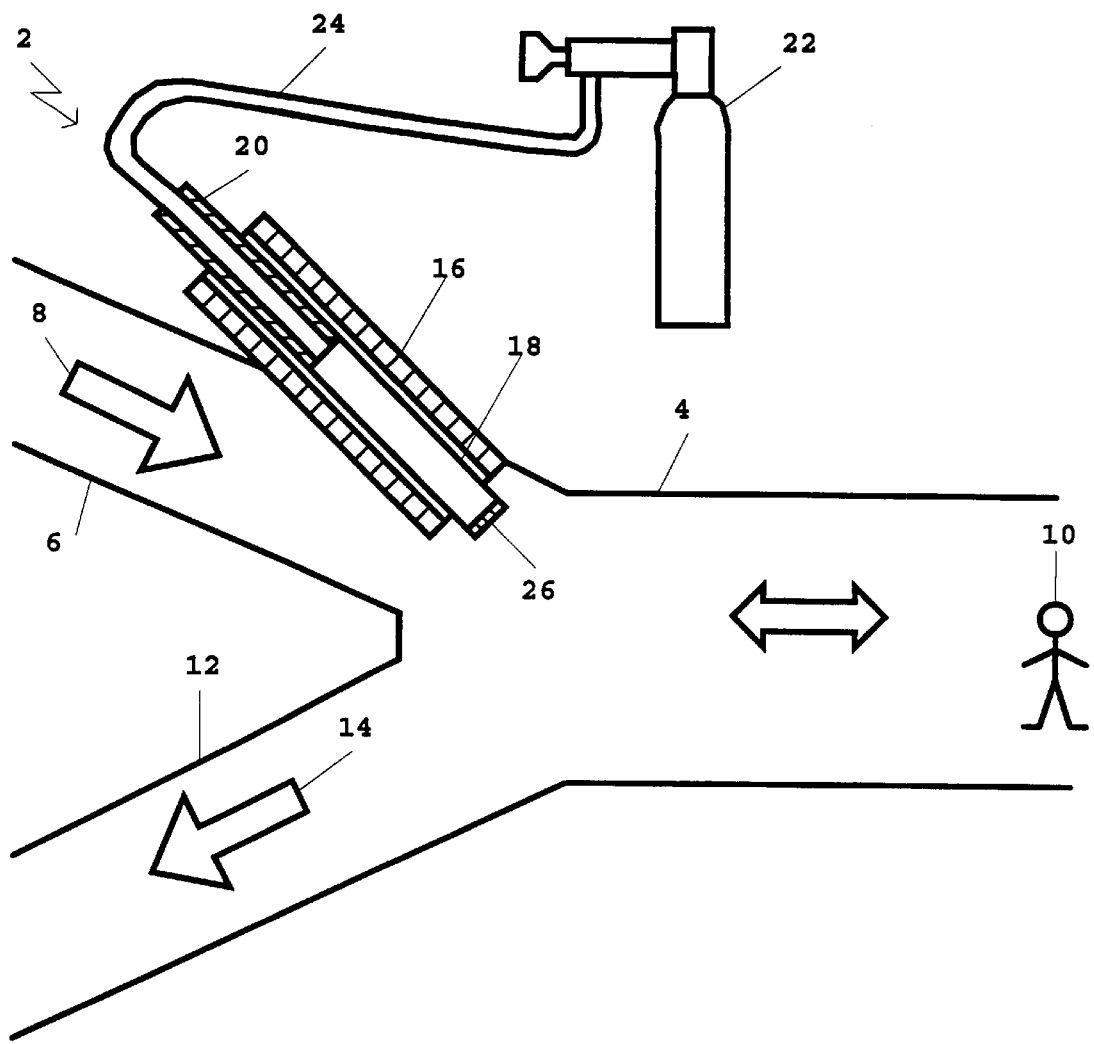
FIG. 1 shows a first embodiment of the dosing according to the invention.

FIG. 1 shows a dosing device 2 intended for use in precision dosing of NO to a patient 10. The dosing device 2 is connected to a Y-piece 4 in a ventilator system (not shown). A breathing gas is supplied, via an inspiratory leg 6 in the Y-piece 4, as the arrow 8 indicates. The breathing gas, to which NO has been added, is carried to the patient 10 through a tracheal tube or in some other known fashion. Gas is carried away from the patient via an expiratory leg 12 in the Y-piece 4, as the arrow 14 indicates.

The actual dosing device 2 includes a tube 16 made of a material impermeable to NO, such as stainless steel. The tube 16 then serves as a barrier means. A membrane tube 18 is movably arranged inside the tube 16. The membrane tube 18 is made of a material permeable to NO, such as Teflon®. The membrane tube 18 is provided with support struts, or some other structure, to stabilize the tube. The membrane tube 18 can be made of a perforated metal tube whose interior is clad with a membrane. This gives the membrane tube 18 a stable structure and reduces the risk of damage to the membrane.

With the aid of a manipulator 20, the membrane tube 18 can be slid back and forth inside the tube 16, thereby exposing a more or less of the diffusion area of the membrane tube 18 to breathing gas in the Y-piece 4. At the same time, a source of gas 22 is connected to the interior of the membrane tube 18 by a gas tube 24. The gas source 22 contains a gas mixture with a specific concentration of NO, e.g. $N_2$ containing 100 ppm of NO. The gas source 22 is suitably regulated so a constant pressure prevails in the membrane tube 18. This results in a constant partial pressure gradient between NO inside and outside the membrane tube 18. Diffusion, governed only by the diffusion area of the membrane tube 18, from the interior of the membrane tube 18 into the breathing gas, is then achieved. Dosing is regulated by exposing an appropriate amount of the total diffusion area. The manipulator 20 and membrane tube 18 can also be devised as a single component.

The manipulator 20 is provided with a scale which designates the active diffusion area, i.e. the amount of NO which diffuses into the breathing gas. If, for example, 1 ppm of NO is desired, the dosing device 2 is set so a 35 corresponding part of the diffusion area of the membrane tube 18 is exposed inside the inspiratory leg 6 of the Y-piece 4.

Breathing gas then picks up NO and conveys it down into the lungs of the patient 10.

The end of the membrane tube 18 is fitted with a plug 26 to prevent the leakage of NO when the membrane tube 18 in the dosing device 2 is completed retracted into the tube 16. The plug is made of stainless steel or some other material impermeable to NO.

Figure 2:
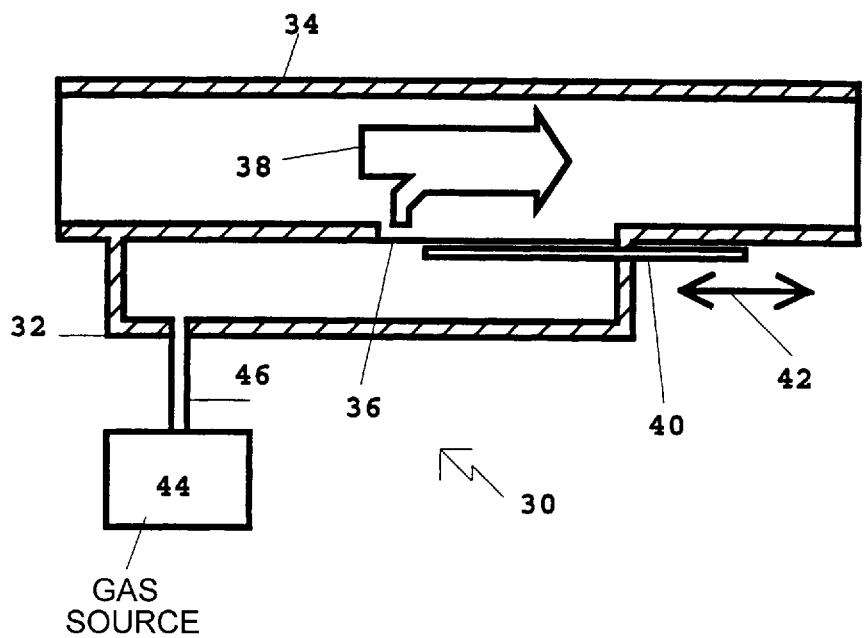
FIG. 2 shows a second embodiment of the dosing according to the invention.

FIG. 2 shows a second embodiment in the form of a dosing device 30. The dosing device 30 includes a container 32, connected to or integral with a tube 34, f or a gas or a liquid. A membrane 36 separates the tube 34 and container 32. A dosing gas in the container 32 can be carried by a gas flowing in the tube 34, as the arrow 38 shows.

A plate 40 is slidingly arranged in the container 32, in front of the membrane 36, to regulate the amount of dosing gas diffusing through the membrane 36. The plate 40, which is made of a material impermeable to the gas, can be moved back and forth, as the arrow 42 shows. A larger or smaller part of the diffusion area of the membrane 36 is then exposed to the gas in the tube 34.

A source of gas 44 is connected to the container 32 by a gas line 46. Constant conditions for the dosing gas in the container 32 can thereby be maintained. As in the preceding embodiment, exact regulation can be achieved by regulating the diffusion area. Regulation can be manual or mechanical. When dosing gases, whose concentrations can be easily measured, are used, a feedback regulatory system can be installed for more accurate control of the diffusion area of the membrane 36.

The plate 40 is appropriately located inside the container 32 when a gas with a positive pressure in relation to the dosing gas flows in the tube 34. The membrane is then pressed against the plate 40 and effects a seal. If the opposite is the case, i.e., if a there is a positive pressure in the container 32 in relation to the gas in the tube 34, the plate 40 should be appropriately located on the exterior of the membrane 36 and container 32. In this embodiment, the plate 40 can also be part of the tube 34 to which the container 32 is connected when dosing is to occur.

In an alternative version of this embodiment, the plate 40 has openings and channels leading to a pump. The pump can be connected to the container 32. When gas is suctioned through the openings, a suction effect is created which presses the membrane 36 again the plate 40. When the plate 40 is shifted to a new position, gas is instead pumped out through the openings. The membrane 36 is blown away from the plate 40 which can then easily be moved to a new position. Position changes can accordingly be made without the risk of damage to the membrane caused by adhesion to or friction against the surface of the plate 40.

Figure 3:
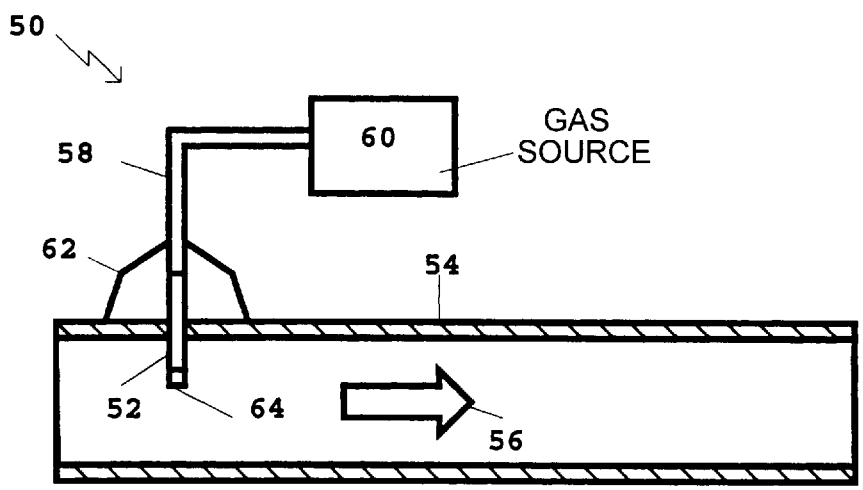
FIG. 3 shows a third embodiment of the dosing according to the invention.

A third embodiment is shown in FIG. 3. The dosing device 50 operates according to the same principle as in the two previously-described embodiments, i.e., dosing is controlled by varying the area of a diffusion surface. The dosing device 50 has a membrane tube 52 which can be connected to a tube 54 for dosing a gas into a carrier gas inside the tube 54. The carrier gas flows in the direction shown by the arrow 56. The membrane tube 52 is connected by a gas line 58 to a source of gas 60. A constant dosing gas pressure is maintained inside the membrane tube 52. Dosing of the dosing gas can be controlled by inserting a larger or smaller part of the membrane tube into the tube 54.

When necessary, a cowl 62 can arranged around the gas line 58 with a gas-tight seal at the junction with the tube 54 to prevent leakage into ambient air. A plug 64 is arranged in the end of the membrane tube 52 to prevent diffusion of dosing gas when the membrane tube 52 is retracted back to the wall of the tube 54.

Figure 4:
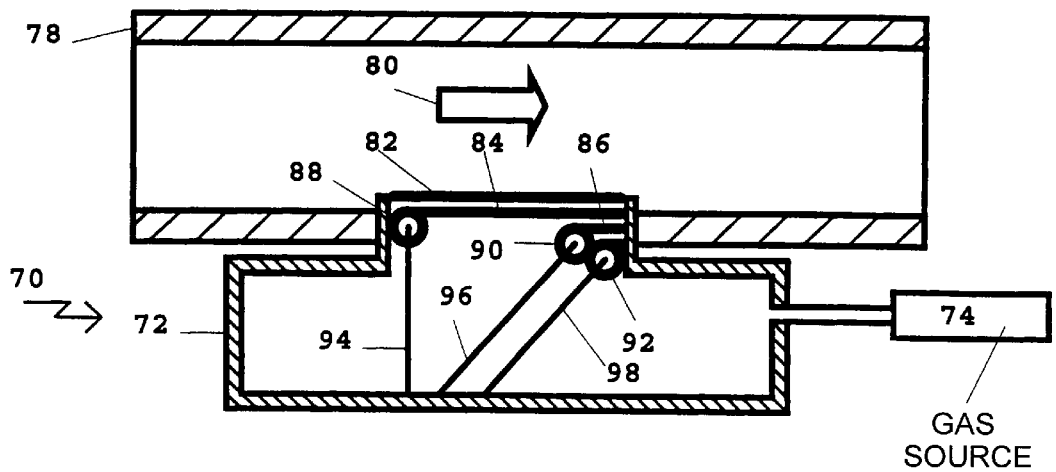
FIG. 4 shows a fourth embodiment of tie dosing according to the invention.

FIG. 4 shows a fourth embodiment of the dosing device, designated 70, according to the invention. This dosing device 70 utilizes another principle for controlling dosing. In this instance, diffusion is controlled by varying the rate of diffusion. The dosing device 70 includes a container 72 connected to a source of gas 74 containing dosing gas. The dosing device 70 is further connected to a tube 78 for dosing gas into a carrier gas in the tube 78. The arrow 80 shows the direction of flow of the gas in the tube 78.

A first membrane 82 is connected to the container 72 so as to separate the interior of the tube 78 from the interior of the container 72. The first membrane 82 is highly permeable to the dosing gas. Inside the first membrane 82, a second membrane 84 is arranged so that it can be rolled out in front of the first membrane 82. The second membrane 84 is wound onto a first roller 88, and the second membrane 84 can be rolled back and forth (as shown in FIG. 4) when a first guide pin 94 is actuated. The second membrane 84 can be arranged so as to press against the first membrane 82 (the distance between the membranes 82 and 84 has been exaggerated in FIG. 4 to illustrate the structure of the dosing device 70). Diffusion can be controlled by regulating the unrolling of the second membrane 84. The second membrane 84 is somewhat less permeable than the first membrane 82, and dosing accordingly decreases as the second membrane 84 is rolled out.

In a corresponding manner, a third membrane 86 is arranged 35 on a second roller 90, and a fourth membrane is arranged on a third roller 92. The third membrane 86 is even less permeable to the dosing gas than the second membrane 84, so dosing can be further reduced (successively) by rolling out increasing amounts of the third membrane 86. This is performed with a second guide pin 96. The fourth membrane is appropriately impermeable to the dosing gas and can successively reduce dosing down to zero. A third guide pin 98 is used to regulate the third roller 92 on which the fourth membrane is arranged.

Figure 5:
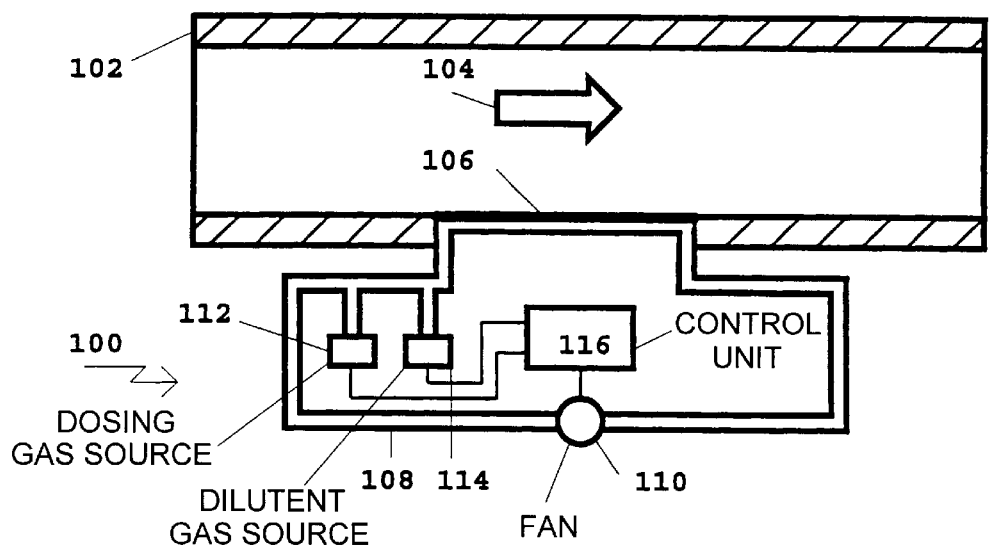
FIG. 5 shows a fifth embodiment of the dosing device according to the invention.

A fifth embodiment, designated 100, of the invention is shown in FIG. 5. The dosing device 100 operates according to yet another principle, however, the dosing device 100, like the previous embodiments, is connected to a tube 102 for dosing a dosing gas into a carrier gas in the tube 102. The carrier gas travels in the direction shown by the arrow 104.

The dosing device 100 includes a membrane 106 which serves as a part of the wall of a tubing system 108. A fan 110 is arranged in the tubing system 108 to force gas through the tubing system 108, causing gas to be continuously exchanged at the membrane 106. A first gas source 112 and a second gas source 114 are connected to the tubing system 108. The first gas source 112 contains the dosing gas, and the second gas source 114 contains a diluent gas. The two gas sources 112 and 114 and the fan 110 are controlled by a control unit 116.

The partial pressure of the dosing gas can be regulated by mixing dosing gas from the first gas source 112 with diluent gas from the second gas source 114. Diffusion through the membrane 106 into the carrier gas in the tube 102 is governed by the partial pressure of the dosing gas. Diffusion and, accordingly, dosing are controlled by regulating the partial pressure of the dosing gas in the tubing system 108.

A continuous flow of dosing gas, corresponding to the quantity diffused, is supplied to the tubing system 108 from the first source of gas 112. Since dosing gas and diluent gas are circulated in the tubing system 108 by the fan 110, the partial pressure of the dosing gas at the membrane 106 is accordingly maintained at the desired level. Partial pressure can also be quickly changed by changing the amount of dosing gas and/or diluent gas supplied.

Figure 6:
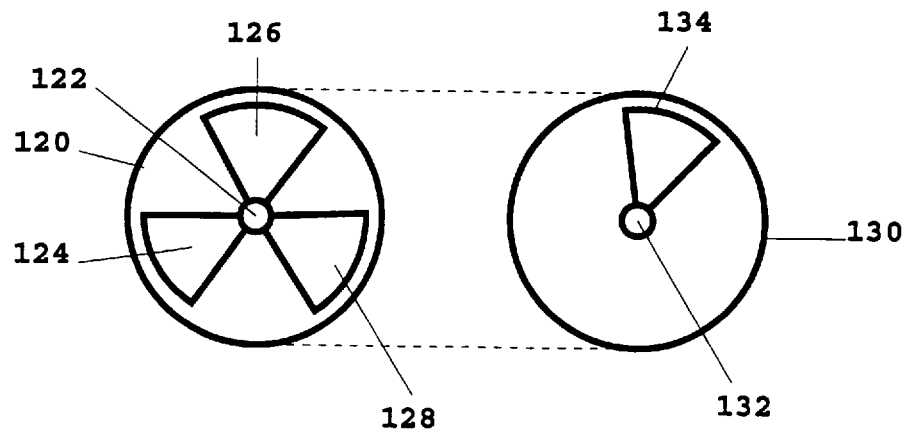
FIG. 6 shows a detail in a sixth embodiment of the device according to the invention.

There are also other ways of controlling diffusion. FIG. 6 shows part of a dosing device which illustrates an additional technique for regulating diffusion. In principle, this apparatus is a combination of some 6f the above embodiments. A first wheel 120 is mounted on a first hub 122. A first membrane 124, a second membrane 126 and a third membrane 128 are arranged in the first wheel 120. The three membranes 124, 126 and 128 have the same shape and size but differing permeabilities to the dosing gas. They are also symmetrically arranged on the first wheel 120. The respective spaces between the membranes 124, 126 and 128 have the same shape as the membranes 124, 126 and 128.

A second wheel 130 is arranged to form a gas-tight seal against the first wheel 120 via second hub 132. The second wheel 130 is made of a material impermeable to the dosing gas. An opening 134 is arranged in the second wheel 130. The size and shape of the opening 134 corresponds to that of each of the three membranes 124, 126, 128.

When the second wheel 130 is rotated in relation to the first wheel 120, an optional amount of any of the membranes 124,126 or 128 can be exposed as a diffusion area for the dosing gas. Rotation can be performed manually or mechanically with a step motor or the like. Mechanical regulation can be controlled by feedback from a dosing gas concentration meter, located on the dosing gas receiver side.

Figure 7:
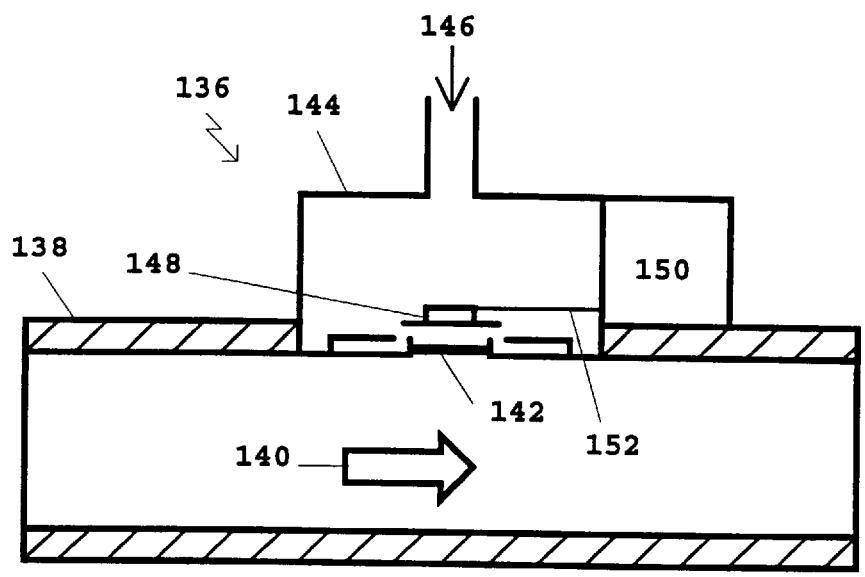
FIG. 7 shows a seventh embodiment of the dosing device according to the invention.

An additional arrangement for the dosing device according to the invention is illustrated in a seventh embodiment, designated 136 in FIG. 7.

The dosing device 136 has a connector tube 138, designed for connection to a flow system for a carrier gas flowing through the connector tube 138, as shown by the arrow 140. A membrane 142 separates the interior of the connector tube 138 from a chamber 144 to which a dosing gas is supplied from a source 146. A valve 148 is arranged near the membrane 142 in the chamber 144. The valve 148 is switched between an open position and a closed position by a control unit 150 via a control line 152.

When the valve 148 is in the open position, dosing gas comes into contact with the membrane 142 and diffuses through the membrane 142 into the carrier gas in the connector tube 138. When the valve 148 is in the closed position, the dosing gas is prevented from coming into contact with the membrane 142. Diffusion through the membrane 142 therefore can be actively controlled by regulating the valve 148 between the open and closed positions. Even if the valve 148 should fail and stick in the open position, dosing is limited by the diffusion capacity of the membrane 142. This makes the dosing device 136 safer than if the valve 148 were used without the membrane 142.

Figure 8:
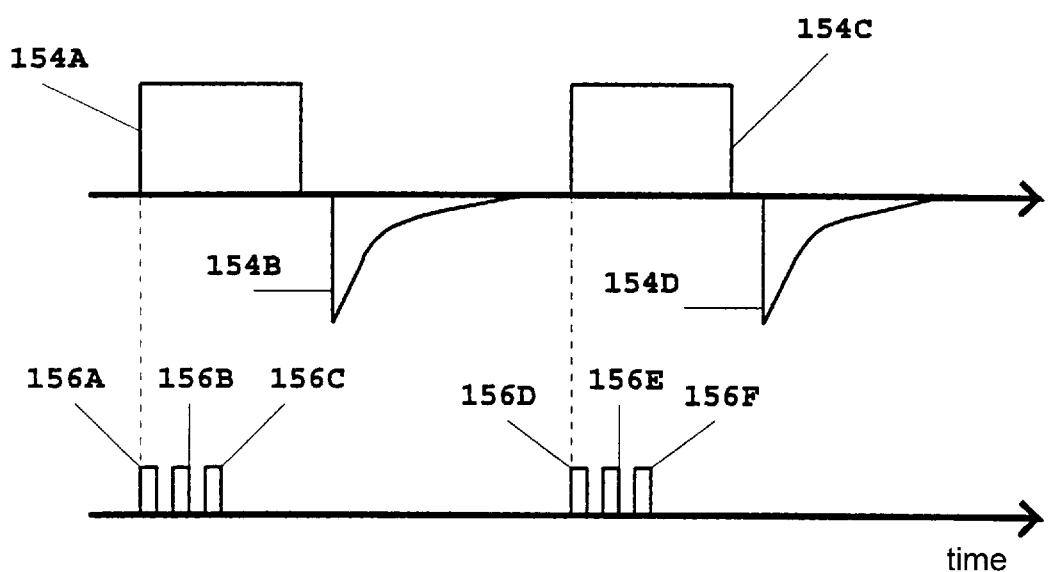
FIG. 8 illustrates a dosing method in accordance with the invention for delivering NO with the dosing device of any of the above embodiments.

One application for the dosing device 136 is illustrated in FIG. 8 in which the dosing device 136 is assumed to be arranged in the inspiratory part of a ventilator system. The ventilator system generates breathing impulses, FIG. 8 (top) showing a first inspiration 154A, a first expiration 154B, a second inspiration 154C and a second expiration 154D.

At the same time as the inspirations 154A and 154C are in progress, a dosing gas, e.g., NO, is supplied in brief pulses 156A–156F. Dosing gas is supplied in such a manner that the control device 150 causes the valve 148 in the dosing device 136 (FIG. 7) to open for a number of brief intervals at the start of each inspiration 154A and 154C. Such pulsed dosing allows a relatively high concentration of NO (when NO is used) to be supplied in the pulses while the total concentration of NO is kept on a lower level (total dilution in the entire breathing gas). Transformation of NO into $NO_2$ is simultaneously minimized.

Numerous versions of the illustrated embodiments can also be easily achieved. For example, the membrane 36 in FIG. 2 can enclose the entire tube 34, and the disk 40 can be replaced with a tube. A number of tubes can be used and moved in different directions to vary the size of the exposure area. The material selected for the membrane depends on the gas to be dosed. For example, Teflon® is appropriate for NO, but there are numerous alternatives, since NO has a high diffusion capacity in many materials.

The described embodiments can be combined with each other in different ways. Dosing gas can be dosed into virtually any kind of container, tube or the like. The membrane can be made of materials selectively permeable to the dosing gas. In some instances, however, the diffusion of other gases in the "opposite direction" may be permissible, but it is most important for dosing gas to diffuse in the "right" direction.

Although only NO is set forth in the above embodiments as the dosing gas, any medical gas could, in principle, be used. The dosing device according to the invention, however, is especially suitable for applications in which the dosing gas and the receiving medium should not come into physical contact (e.g., -o prevent over-dosing or to minimize chemical reactions). There are numerous applications in the medical field other than the dosing of NO, e.g. the dosing of other gaseous medication or anesthetic into a breathing gas.

The container for the dosing gas does not need to be connected to a source of gas containing the dosing gas. In instances in which the dosing gas is an anesthetic gas, the anesthetic can be in the liquid state in the container, and a constant partial pressure for the anesthetic gas is maintained at the membrane by controlling the liquid anesthetic's temperature. Solid materials which emit a medical gas relatively constantly can be used as a source of gas.

Although modifications and changes may be suggested by those skilled in the art, it is the intention of the inventor to embody within the patent warranted hereon all changes and modifications as reasonably and properly come within the scope of his contribution to the art.

I claim as my invention:

1. A dosing device comprising:
   a gas container containing a gas;
   a fluid container containing a fluid;
   at least one membrane separating said gas from said fluid and having an active area with a permeability include means for permitting a variable amount of said gas to diffuse through said active area into said fluid; and
   means for controlling diffusion of said gas through said active area by varying said amount of said gas diffused through said active area into said fluid.

2. A dosing device as claimed in claim 1 wherein said gas comprises NO and said fluid comprises respiratory air and wherein said fluid container comprises means adapted for delivering said respiratory gas with said dosage of NO therein to a respirating subject.

3. A dosing device as claimed in claim 1 wherein said means for controlling diffusion comprises means for varying a size of said active area.

4. A dosing device as claimed in claim 3 further comprising means for maintaining a constant partial pressure of said gas in said gas container.

5. A dosing device as claimed in claim 3 further comprising a barrier movably disposed relative to said active area, and wherein said means for varying said size of said active area comprises means for producing relative movement between said barrier and said membrane for exposing more or less of said active area.

6. A dosing device as claimed in claim 5 wherein said barrier comprises a tube having an end in contact with said fluid, and wherein said gas container comprises a tubular cylinder, slidable inside said tube, said membrane comprising at least a portion of an exterior of said cylinder, the size of said active area being varied as said cylinder advances beyond said end of said tube.

7. A dosing device as claimed in claim 5 wherein said gas container includes a chamber having an opening, covered by said membrane, placing said chamber in communication with said fluid, and wherein said barrier comprises a plate, and wherein said means for varying the size of said active area comprises means for sliding said plate over said membrane to expose more or less of said membrane.

8. A dosing device as claimed in claim 1 wherein said membrane comprises a membrane with a variable permeability to said gas, and wherein said means for controlling diffusion comprises means for varying said permeability of said membrane.

9. A dosing device as claimed in claim 8 further comprising means for maintaining a constant partial pressure of said gas in said gas container.

10. A dosing device as claimed in claim 8 wherein said membrane comprises a plurality of coatings, each coating having a different permeability to said gas, and wherein said means for controlling diffusion comprises means for selectively combining said coatings in said active area.

11. A dosing device as claimed in claim 1 wherein said gas container includes a chamber having an opening, covered by said membrane, placing said chamber in communication with said fluid, said membrane comprising a plurality of sheets, each sheet being rolled on a roller, and wherein said means for controlling diffusion comprises means for unrolling a selected number of said sheets to cover said opening.

12. A dosing device as claimed in claim 11 further comprising means for maintaining a constant partial pressure of said gas in said gas container.

13. A dosing device as claimed in claim 1 wherein said means for controlling diffusion comprises valve means, disposed adjacent said membrane, for, in a closed position, preventing said gas from coming into contact with said diffusion area and for, in an open position, allowing dosing gas to come into contact with said diffusion area, and means for regulating a time during which said valve means remains in said open position for controlling diffusion of said gas through said membrane.

14. A dosing device as claimed in claim 13 further comprising means for maintaining a constant partial pressure of said gas in said gas container.

15. A dosing device as claimed in claim 1 further comprising means for maintaining a constant partial pressure of said gas in said gas container.

16. A dosing device as claimed in claim 1 wherein said gas in said gas container is at a partial pressure, and wherein said means for controlling diffusion comprises means for regulating said partial pressure of said gas.

17. A dosing method comprising the steps of:
    containing a gas in a gas container;
    containing a fluid in a fluid container;
    separating said gas from said fluid by at least one membrane having an active area with a permeability and permitting a variable amount of said gas to diffuse through said active area into said fluid; and
    controlling diffusion of said gas through said active area by varying said amount of said gas diffused through said active area into said fluid.

18. A dosing method as claimed in claim 17 wherein said gas comprises NO and said fluid comprises respiratory air and comprising the additional step of delivering said respiratory gas with said dosage of NO therein to a respirating subject.

19. A dosing method as claimed in claim 17 wherein the steps of controlling diffusion comprises varying a size of said active area.

20. A dosing method as claimed in claim 19 comprising the additional step of maintaining a constant partial pressure of said gas in said gas container.

21. A dosing method as claimed in claim 19 comprising the additional step of movably disposing a barrier relative to said active area, and wherein the steps of varying said size of said active area comprises producing relative movement between said barrier and said membrane for exposing more or less of said active area.

22. A dosing method as claimed in claim 21 wherein said barrier comprises a tube having an end in contact with said fluid, and wherein said gas container comprises a tubular cylinder, slidable inside said tube, said membrane comprising at least a portion of an exterior of said cylinder, and wherein the step of varying said size of said active area comprises varying the size of said active area by advancing said cylinder beyond said end of said tube.

23. A dosing method as claimed in claim 21 wherein said gas container includes a chamber having an opening, covered by said membrane, placing said chamber in communication with said fluid, and wherein said barrier comprises a plate, and wherein the step of varying the size of said active area comprises sliding said plate over said membrane to expose more or less of said membrane.

24. A dosing method as claimed in claim 17 wherein said membrane comprises a membrane with a variable permeability to said gas, and wherein the step of controlling diffusion comprises means for varying said permeability of said membrane.

25. A dosing method as claimed in claim 24 comprising the additional step of maintaining a constant partial pressure of said gas in said gas container.

26. A dosing method as claimed in claim 24 wherein said membrane comprises a plurality of coatings, each coating having a different permeability to said gas, and wherein the step of controlling diffusion comprises selectively combining said coatings in said active area.

27. A dosing method as claimed in claim 17 wherein said gas container includes a chamber having an opening, covered by said membrane, placing said chamber in communication with said fluid, said membrane comprising a plurality of sheets, and comprising the additional step of rolling each sheet on a roller, and wherein the step of controlling diffusion comprises unrolling a selected number of said sheets to cover said opening.

28. A dosing method as claimed in claim 27 comprising the additional step of maintaining a constant partial pressure of said gas in said gas container.

29. A dosing method as claimed in claim 17 comprising the additional steps of disposing a valve adjacent said membrane, said valve, in a closed position, preventing said gas from coming into contact with said diffusion area and in an open position, allowing dosing gas to come into contact with said diffusion area, and wherein the step of controlling diffusion comprises regulating a time during which said valve remains in said open position.

30. A dosing method as claimed in claim 29 comprising the additional step of maintaining a constant partial pressure of said gas in said gas container.

31. A dosing method as claimed in claim 17 further comprising the additional step of maintaining a constant partial pressure of said gas in said gas container.

32. A dosing method as claimed in claim 17 wherein said gas in said gas container is at a partial pressure, and wherein the step of controlling diffusion comprises regulating said partial pressure of said gas.

* * * * *